(12) United States Patent
Fife et al.

(10) Patent No.: US 8,796,036 B2
(45) Date of Patent: Aug. 5, 2014

(54) METHOD AND SYSTEM FOR DELTA DOUBLE SAMPLING

(75) Inventors: Keith Fife, Palo Alto, CA (US); Jungwook Yang, Newton, MA (US)

(73) Assignee: Life Technologies Corporation, Carlsbad, CA (US)

(*) Notice: Subject to any disclaimer, the term of this patent is extended or adjusted under 35 U.S.C. 154(b) by 667 days.

(21) Appl. No.: 13/173,851

(22) Filed: Jun. 30, 2011

(65) Prior Publication Data

US 2012/0074956 A1 Mar. 29, 2012

Related U.S. Application Data

(60) Provisional application No. 61/386,403, filed on Sep. 24, 2010.

(51) Int. Cl.
*G01N 15/06* (2006.01)
*G01N 27/414* (2006.01)

(52) U.S. Cl.
CPC ......... *G01N 27/4148* (2013.01); *Y10S 436/806* (2013.01); *Y10S 436/807* (2013.01)
USPC .............. 436/149; 422/68.1; 422/98; 436/43; 436/150; 436/151; 436/806; 436/807

(58) Field of Classification Search
USPC .......... 422/68.1, 98, 82.01; 436/43, 149, 150, 436/151, 806, 807
See application file for complete search history.

(56) References Cited

U.S. PATENT DOCUMENTS

| | | |
|---|---|---|
| 4,086,642 A | 4/1978 | Yoshida et al. |
| 4,411,741 A | 10/1983 | Janata |
| 4,437,969 A | 3/1984 | Covington et al. |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |

(Continued)

FOREIGN PATENT DOCUMENTS

| | | |
|---|---|---|
| CN | 102203282 | 9/2011 |
| DE | 19512117 | 10/1996 |

(Continued)

OTHER PUBLICATIONS

Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.

(Continued)

*Primary Examiner* — Brian J Sines

(57) ABSTRACT

An array of sensors arranged in matched pairs of transistors with an output formed on a first transistor and a sensor formed on the second transistor of the matched pair. The matched pairs are arranged such that the second transistor in the matched pair is read through the output of the first transistor in the matched pair. The first transistor in the matched pair is forced into the saturation (active) region to prevent interference from the second transistor on the output of the first transistor. A sample is taken of the output. The first transistor is then placed into the linear region allowing the sensor formed on the second transistor to be read through the output of the first transistor. A sample is taken from the output of the sensor reading of the second transistor. A difference is formed of the two samples.

11 Claims, 6 Drawing Sheets

(56) References Cited

U.S. PATENT DOCUMENTS

| | | |
|---|---|---|
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,038,192 A | 8/1991 | Bonneau |
| 5,110,441 A | 5/1992 | Kinlen et al. |
| 5,113,870 A | 5/1992 | Rossenfeld |
| 5,138,251 A | 8/1992 | Koshiishi et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,490,971 A | 2/1996 | Gifford et al. |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Park et al. |
| 6,538,593 B2 | 3/2003 | Yang et al. |
| 6,545,620 B2 | 4/2003 | Groeneweg |
| 6,602,702 B1 | 8/2003 | McDevitt et al. |
| 6,605,428 B2 | 8/2003 | Klinger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,700,814 B1 | 3/2004 | Nahas et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,888,194 B2 | 5/2005 | Yoshino |
| 6,919,211 B1 | 7/2005 | Fodor et al. |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakov et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,359,058 B2 | 4/2008 | Kranz et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,455,971 B2 | 11/2008 | Chee et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,482,153 B2 | 1/2009 | Okada et al. |
| 7,515,124 B2 | 4/2009 | Yaguma et al. |
| 7,575,865 B2 | 8/2009 | Leamon et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,303 B1 | 10/2009 | Lee |
| 7,612,817 B2 | 11/2009 | Tay |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,785,790 B1 | 8/2010 | Church et al. |
| 7,859,029 B2 | 12/2010 | Lee et al. |
| 7,885,490 B2 | 2/2011 | Heideman et al. |
| 7,888,013 B2 | 2/2011 | Miyahara et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 7,981,362 B2 | 7/2011 | Glezer et al. |
| 8,067,731 B2 | 11/2011 | Matyjaszczyk et al. |
| 8,124,936 B1 | 2/2012 | Lagna |
| 8,199,859 B2 | 6/2012 | Zerbe et al. |
| 8,217,433 B1 | 7/2012 | Fife |
| 8,231,831 B2 | 7/2012 | Hartzell et al. |
| 8,247,849 B2 | 8/2012 | Fife et al. |

(56) References Cited

U.S. PATENT DOCUMENTS

| | | |
|---|---|---|
| 8,262,900 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,426,898 B2 | 4/2013 | Rothberg et al. |
| 8,449,824 B2 | 5/2013 | Sun |
| 8,558,288 B2 | 10/2013 | Rothberg et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0150909 A1 | 10/2002 | Stuelpnagel et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0044799 A1 | 3/2003 | Matson |
| 2003/0049624 A1 | 3/2003 | Schultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0124572 A1 | 7/2003 | Umek et al. |
| 2003/0124599 A1 | 7/2003 | Chen et al. |
| 2003/0138809 A1 | 7/2003 | Williams et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0157504 A1 | 8/2003 | Chee et al. |
| 2003/0186262 A1 | 10/2003 | Cailloux et al. |
| 2003/0194740 A1 | 10/2003 | Williams |
| 2003/0211502 A1 | 11/2003 | Sauers et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0134798 A1 | 7/2004 | Toumazou et al. |
| 2004/0136866 A1 | 7/2004 | Pontis et al. |
| 2004/0185484 A1 | 9/2004 | Costa et al. |
| 2004/0197803 A1 | 10/2004 | Yaku et al. |
| 2004/0207384 A1 | 10/2004 | Brederlow et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1 | 6/2005 | Glezer et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0231824 A1 | 10/2007 | Chee et al. |
| 2007/0233477 A1 | 10/2007 | Halowani et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0186093 A1 | 8/2008 | Forbes |
| 2008/0197022 A1 | 8/2008 | Suzuki et al. |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286762 A1 | 11/2008 | Miyahara et al. |

(56) References Cited

U.S. PATENT DOCUMENTS

| | | |
|---|---|---|
| 2008/0286767 A1 | 11/2008 | Miyahara et al. |
| 2009/0026082 A1 | 1/2009 | Rothberg et al. |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0127589 A1 | 5/2009 | Rothberg et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0001779 A1 | 1/2012 | Fife et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0074956 A1 | 3/2012 | Fife et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0173159 A1 | 7/2012 | Davey et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| DE | 102008012899 | 9/2009 |
| EP | 1975246 | 3/1984 |
| EP | 0223618 | 5/1987 |
| EP | 1371974 | 12/2003 |
| EP | 1432818 | 6/2004 |
| EP | 1542009 | 6/2005 |
| EP | 1557884 | 7/2005 |
| EP | 1870703 | 12/2007 |
| EP | 2307577 | 4/2011 |
| GB | 2457851 | 9/2009 |
| GB | 2461127 B | 7/2010 |
| JP | 2000055874 | 2/2000 |
| JP | 2002272463 | 9/2002 |
| JP | 2005218310 | 8/2004 |
| JP | 2005-518541 | 6/2005 |
| JP | 2005518541 | 6/2005 |
| JP | 2011-525810 | 9/2011 |
| KR | 10-0442838 | 7/2004 |
| KR | 10-0455283 | 10/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/42498 | 6/2001 |
| WO | WO-01/81896 | 11/2001 |
| WO | WO-02/077287 | 10/2002 |
| WO | WO-02/086162 | 10/2002 |
| WO | WO-03/073088 | 9/2003 |
| WO | WO-2004/040291 | 5/2004 |
| WO | WO2004040291 | 5/2004 |
| WO | WO2004048962 | 6/2004 |
| WO | WO2005015156 | 2/2005 |
| WO | WO-2005/047878 | 5/2005 |
| WO | WO2005043160 | 5/2005 |
| WO | WO2005602049 | 7/2005 |
| WO | WO-2005/084367 | 9/2005 |
| WO | WO2005090961 | 9/2005 |
| WO | WO-2006/005967 | 1/2006 |
| WO | WO-2006/022370 | 3/2006 |
| WO | WO2007002204 | 1/2007 |
| WO | WO-2007/086935 | 8/2007 |
| WO | WO-2008/007716 | 1/2008 |
| WO | WO-2008/058282 | 5/2008 |
| WO | WO-2008/076406 | 6/2008 |
| WO | WO-2008/107014 | 9/2008 |
| WO | WO-2009/012112 | 1/2009 |
| WO | WO2009041917 | 4/2009 |
| WO | WO2009074926 | 6/2009 |
| WO | WO2009081890 | 7/2009 |
| WO | WO-2009/158006 | 12/2009 |
| WO | WO-2010/008480 | 1/2010 |
| WO | WO-2010/047804 | 4/2010 |
| WO | WO-2010/047804 A8 | 4/2010 |
| WO | WO-2010/138182 | 12/2010 |
| WO | WO-2010/138188 | 12/2010 |
| WO | WO-2012/003359 | 1/2012 |
| WO | WO-2012/003363 | 1/2012 |
| WO | WO-2012/003368 | 1/2012 |

(56) References Cited

FOREIGN PATENT DOCUMENTS

| WO | WO-2012/003380 | 1/2012 |
|----|----------------|--------|
| WO | WO-2012/006222 | 1/2012 |
| WO | WO2012003359   | 1/2012 |

OTHER PUBLICATIONS

EP09798251.6 Extended European Search Report dated Aug. 27, 2013.
EP11801437.2 Extended European Search Report dated Jul. 25, 2013.
EP11804218.3 Extended European Search Report dated Jul. 11, 2013.
EP11804218.3 First Office Action dated Jul. 29, 2013.
EP11827128.7 European Search Report dated Aug. 1, 2013.
EP13161312.7 Extended European Search Report dated Oct. 15, 2013.
EP13163995.7 Extended European Search Report dated Aug. 20, 2013.
EP13163995.7 First Office Action dated Aug. 30, 2013.
EP13164768.7 Extended European Search Report dated Aug. 20, 2013.
EP13164768.7 First Office Action dated Aug. 30, 2013.
Eriksson, J. et al. "Pyrosequencing Technology at Elevated Temperature" Electrophoresis, vol. 25, 2004, pp. 20-27.
Hanshaw, R. et al., "An indicator displacement system for fluorescent detection of phosphate oxyanions under physiological conditions" Science Direct, Tetrahedron Ltrs., vol. 45, 2004, pp. 8721-8724.
Hizawa, et al. "Sensing Characteristics of Charge Transfer Type pH Sensor by Accumulative Operation" IEEE Sensors, EXCO, Daegu, Korea, 2006, pp. 144-147.
JP20120246413 First Office Action dated Jun. 28, 2013.
Lee, S. et al. "An Enhanced Glucose Biosensor Using Charge Transfer Techniques" Biosensors and Bioelectronics, vol. 24, 2008, pp. 650-656.
Maki, W et al., "Nanowire-transistor based ultra-sensitive DNA methylation detection", Biosensors & Bioelectronics, vol. 23, 2008, pp. 780-787.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Milgrew, M. et al. "A Proton Camera Array Technology for Direct Extracellular Ion Imaging" IEEE International Symposium on Industrial Electronics, 2008, pp. 2051-2255.
PCT/US2011/042683 International Preliminary Report on Patentability Mailed Jun. 4, 2013.
PCT/US2013/022129 International Search Report and Written Opinion dated Aug. 9, 2013.
Premanode, B. et al. "Drift Reduction in Ion-Sensitive FETs Using Correlated Double Sampling", Electronics Letters, IEEE Stevenage, GB, vol. 43 (16) Aug. 2, 2007.
Rothberg, J. et al., "An integrated semiconductor device enabling non-optical genome sequencing" Nature, vol. 475, No. 7356, 2011, pp. 348-352.
Sawada, K. et al., "Highly sensitive ion sensors using charge transfer technique", Sensors Actuators B, vol. 98, 2004, pp. 69-72.
Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.
Voigt, H. et al. "Diamond-like carbon-gate pH-ISFET" Sensors and Actuators B., vol. 44, 1997, pp. 441-445.
EP13174555.6 EP Extended Search Report Dec. 12, 2013.
EP13174555.6 EP Search Report Nov. 21, 2013.
EP13177039.8 EP Search Report Nov. 21, 2013.
EP13177590.0 EP Search Report Nov. 20, 2013.
Hammond, et al. "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.
Wood, et al. "Base composition-independent hybridization in tetramethylammonium chloride: a method for oligonucleotide screening of highly complex gene libraries" Proc. Nat. Acad. Sci., 1985, pp. 1585-1588.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chinese Patent Application 200780051353.2 Second Office Action Mailed Mar. 5, 2013.
Chung, W-Y. et al., "New ISFET Interface Circuit Design with Temperature Compensation", Microelectronics Journal, vol. 37(10), 2006, pp. 1105-1114.
Chung, W-Y. et al., "Temperature Compensation Electronics for ISFET Readout Applications", Biomedical Circuits and Systems, IEEE International Workshop Singapore, 2004, pp. 305-308.
JP2012246413 First Office Action Mailed Jun. 28, 2013.
Krause, M. et al., "Extended Gate Electrode Arrays for Extracellular Signal Recordings", Sensors and Actuators B, vol. 70, 2000, pp. 101-107.
Park, K-Y. et al., "ISFET Glucose Sensor System With Fast Recovery Characteristics by Employing Electrolysis", Sensors and Actuators B: Chemical, vol. 83 (1-3), 2002, pp. 90-97.
PCT/US2010/048835 International Preliminary Report on Patentability Mailed Mar. 19, 2013.
PCT/US2011/042668 International Preliminary Report on Patentability Mailed Mar. 26, 2013.
PCT/US2012/058996 International Search Report and Written Opinion Mailed Jan. 22, 2013.
PCT/US2012/071471 International Search Report and Written Opinion Mailed Apr. 24, 2013.
PCT/US2012/071482 International Search Report and Written Opinion Mailed May 23, 2013.
PCT/US2013/022140 International Search Report and Written Opinion Mailed May 2, 2013.
Pollack, J. et al. "Genome-Wide Analysis of DNA copy-number changes using cDNA Microarrays", Nature Genetics, vol. 23, 1999, pp. 41-46.
[No Author Listed], "ISFET Wikipedia article", *Wikipedia*, Last modified Nov. 7, 2006.
Ahmadian, A. et al., "Single-nucleotide polymorphism analysis by pyrosequencing", *Anal. Biochem*, vol. 280, 2000, pp. 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767 Search Information Statement Mailed Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M. et al., "Fully electronic DNA hybridization detection by a standard CMOS biochip", *Sensors and Actuators B Chemical*, vol. 118, 2006, pp. 41-46.
Bashford, G. et al., "Automated bead-trapping apparatus and control system for single-molecule DNA sequencing", *Optics Express*, vol. 16(5), Mar. 3, 2008, pp. 3445-3455.
Baumann, W. et al., "Microelectronic sensor system for microphysiological application on living cells", *Sensors Actuators B*, vol. 55, 1999, pp. 77-89.
Bausells, J. et al., "Ion-sensitive field-effect transistors fabricated in a commercial CMOS technology", *Sensors and Actuators B Chemical*, vol. 57, 1999, pp. 56-62.
Bergveld, P., "ISFET, Theory and Practice", *IEEE Sensor Conference*, Toronto, Oct. 2003, 2003, pp. 1-26.

(56) References Cited

OTHER PUBLICATIONS

Bergveld, P., "Thirty years of ISFETOLOGY What happened in the past 30 years and what may happen in the next 30 years", *Sensors and Actuators B*, vol. 88, 2003, pp. 1-20.
Besselink, G et al., "ISFET Affinity Sensor", *Methods in Biotechnology*, vol. 7: *Affinity Biosensors: Techniques and Protocols*, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.
Bousse, L. et al., "A process for the combined fabrication of ion sensors and CMOS circuits", *IEEE Electron Device Letters*, vol. 9(1), 1988, pp. 44-46.
Bousse, L. et al., "Zeta potential measurements of Ta2O5 and SiO2 thin films", *J. Colloid Interface Sci.*, vol. 147(1), 1991, pp. 22-32.
Chen, Y. et al., "Nanoscale field effect transistor for biomolecular signal amplification", *App Phys Letter.*, vol. 91, 2007, pp. 243511-1-243511-3.
Chen, Y. et al., "Silicon-based nanoelectronic field-effect pH sensor with local gate control", *App Phys Letter*, vol. 89, 2006, pp. 223512-1-223512-3.
Chou, J. et al., "Letter to the Editor on Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-76.
Chung, W-Y et al., "ISFET interface circuit embedded with noise rejection capability", *Electronics Letters.*, vol. 40(18), e-pub; 2 pages, 2004.
Chung, W-Y et al., "ISFET performance enhancement by using the improved circuit techniques", *Sensors and Actuators B*, vol. 113, 2006, pp. 555-562.
Eijkel, J. et al., "Measuring Donnan-related phenomena using a solid-state ion sensor and a concentration-step method", *J. Membrane Sci.*, vol. 127, 1997, pp. 203-221.
Eijkel, J., "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662.
EP7867780.4 Examination Report Mailed Jul. 3, 2012.
Eriksson, J. et al., "Pyrosequencing technology at elevated temperature", *Electrophoresis*, vol. 25, 2004, pp. 20-27.
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico Jun. 18-20, 2007, pp. 1-5.
Eversmann, B. et al., "A 128 × 128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J, "Handbook of Modern Sensors—Physics, Designs, and Applications . . . ", *17.3.2 CHEMFET Sensors*, 1996, pp. 499-501.
Fritz, J. et al., "Electronic detection of DNA by its intrinsic molecular charge", *PNAS*, vol. 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", *Proc IEEE 1992 Intl Conf Microelec Test Struct*, vol. 5, 1992, pp. 156-159.
Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P. et al., "Design of a Single-Chip pH Sensor Using a Conventional 0.6—μm CMOS Process", *IEEE Sensors Journal*, vol. 4(6), 2004, pp. 706-712.
Hammond, P. et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hampster ovary cell line using Illumina sequencing technology", *BMC Genomics*, vol. 12:67, 2011, pp. 1-8.
Han, Y, "Label-free detection of biomolecules by a field-effect transistor microarray biosensor with bio-functionalized gate surfaces," Masters Dissertation, 2006, pp. 1-63.
Hara, H. et al., "Dynamic response of a Ta205-gate pH-sensitive field-effect transistor", *Sensors Actuators B*, vol. 32, 1996, pp. 115-119.
Hermon, Z. et al., "Miniaturized bio-electronic hybrid for chemical sensing applications", *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, M. et al., "Identification of a Single Nucleotide Polymorphism in the MXA Gene Promoter (T/T at nt -88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, 117, 2006, pp. 509-515.
Hizawa, T. et al., "32 × 32 pH Image Sensors for Real Time Observation of Biochemical Phenomena", *Transducers & Eurosensors '07*, 14th Intl. Conf. on Solid-State, Actuators and Microsystems, Lyon, France, Jun. 10-14, 2007, 2007, pp. 1311-1312.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact image for locating individual cells", *ISCAS*, 2006, pp. 3357-3360.
Ji, H. et al., "Contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), 2004, pp. 69-74.
Klein, M., "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.
Leamon, J. et al., "Cramming More Sequencing Reactions onto Microreactor Chips", *Chemical Reviews*, vol. 107, 2007, pp. 3367-3376.
Lee, C-S et al., "Ion-sensitive Field-Effect Transistor for Biological Sensing", *Sensors*, vol. 9, 2009, pp. 7111-7131.
Li, et al., "Sequence-Specific Label-Free DNA Sensors Based on Silico Nanowires", *Nano Letters* vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proceedings of the 1996 IEEE International Conference on Microelectronic Test Structures*, vol. 9, 1996, pp. 123-128.

(56) References Cited

OTHER PUBLICATIONS

Margulies, M. et al., "Genome sequencing in microfabricated high-density picolitre reactors", *Nature*, vol. 437(7057), 2005, pp. 376-380.
Marshall, A. et al., "DNA chips: an array of possibilities", *Nature Biotechnology*, vol. 16, 1998, pp. 27-31.
Martinoia, S. et al., "A behavioral macromodel of the ISFET in SPICE", *Sensors Actuators B*, vol. 62, 2000, pp. 182-189.
Martinoia, S., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), 2006, pp. 1037-1044.
Milgrew, M. et al., "A 16 × 16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "A large transistor based sensor array chip for direct extracellular imaging", *Sensors and Actuators B Chemical*, vol. 111-112, 2005, pp. 347-353.
Milgrew, M. et al., "Matching the transconductance characteristics of CMOS ESFET arrays by removing trapped charge", *IEEE Trans Electron Devices*, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", *Sensors and Actuators B*, vol. 103, 2004, pp. 37-42.
Milgrew, M. et al., "The fabrication of scalable multi-sensor arrays using standard CMOS technology", *2003 IEEE Custom Integrated Circuits Conference*, 2003, pp. 513-516.
Miyahara, Y. et al., "Biochip Using Micromachining Technology", *J. Institute of Electrostatics*, Japan, vol. 27(6), 2003, pp. 268-272.
Miyahara, Y. et al., "Direct Transduction of Primer Extension into Electrical Signal Using Genetic Field Effect Transistor", *Micro Total Analysis Systems 2004*, vol. 1, 2004, pp. 303-305.
Miyahara, Y. et al., "Potentiometric Detection of DNA Molecules Using Field Effect Transistor", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, pp. 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), 2006, pp. 4261-4269.
PCT/JP2005/001987 International Search Report Mailed Apr. 5, 2005.
PCT/JP2005/015522 International Preliminary Report on Patentability Mailed Mar. 19, 2007.
PCT/JP2005/015522 International Search Report Mailed Sep. 27, 2005.
PCT/US/2009/05745 International Preliminary Report on Patentability Issued Apr. 26, 2011.
PCT/US/2009/05745 International Search Report Mailed Dec. 11, 2009.
PCT/US/2009/05745 Written Opinion Mailed Dec. 11, 2009.
PCT/US2010/01547 International Preliminary Report on Patentability Mailed Nov. 29, 2011.

PCT/US2007/025721 Declaration of Non-Establishment of International Search Report Mailed Jul. 15, 2008.
PCT/US2007/025721 International Preliminary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011, pp. 1-8.
PCT/US2010/001543 International Search Report and Written Opinion Mailed Oct. 13, 2010, pp. 1-12.
PCT/US2010/001553 International Preliminary Report on Patentability Mailed Dec. 8, 2011, pp. 1-10.
PCT/US2010/001553 International Search Report Mailed Jul. 28, 2010, pp. 1-2.
PCT/US2010/001553 Written Opinion Mailed Jul. 14, 2010, pp. 1-6.
PCT/US2010/48835 International Search Report and Written Opinion Mailed Dec. 16, 2010, pp. 1-12.
PCT/US2011/042655 International Search Report Mailed Oct. 21, 2011, pp. 1-2.
PCT/US2011/042660 International Search Report Mailed Nov. 2, 2011.
PCT/US2011/042665 International Search Report Mailed Nov. 2, 2011.
PCT/US2011/042668 International Search Report Mailed Oct. 28, 2011.
PCT/US2011/042669 International Search Report Mailed Jan. 9, 2012, pp. 1-5.
PCT/US2011/042669 Written Opinion Mailed Jan. 9, 2012, pp. 1-5.
PCT/US2011/042683 International Search Report Mailed Feb. 16, 2012.
PCT/US2011/042683 Written Opinon Mailed Feb. 16, 2012.
Poghossian, A. et al., "Functional testing and characterization of ISFETs on wafer level by means of a micro-droplet cell", *Sensors*, vol. 6, 2006, pp. 397-404.
Pourmand, N et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Ultra-low power precision ISFET readout using global current feedback", *Electronic Lett*, vol. 42(22), 2006, 2 pages.
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968.
Purushothaman, S. et al., "Towards Fast Solid State DNA Sequencing", *IEEE ISCAS 2002 Proceedings*, Circuits and Systems, vol. 4, 2002, pp. IV-169-IV-172.
Rodriguez-Villegas, E., "Solution to trapped charge in FGMOS transistors", *Electronics Letters*, vol. 39(19), 2003.
Ronaghi, M. et al., "A Sequencing Method Based on Real-Time Pyrophosphate", *Science*, vol. 281, 1998, pp. 363-365.
Sakata, T. et al., "Cell-based field effect devices fo cell adhesion analysis", *Intl. Conf. on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proc. of*

(56) References Cited

OTHER PUBLICATIONS

*2006 Intl. Conf. on Microtechnologies in Medicine and Biology*, May 9-12, 2005, Okinawa, Japan, 2006, pp. 97-100.

Sakata, T. et al., "Direct detection of single nucleotide polymorphism using genetic field effect transistor", *Digest of Papers Microprocesses and Nanotechnology 2004, Osaka, Japan*, 2004 Intl. Microprocesses and Nanotechnology Conf., 2004, pp. 226-227.

Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, 2005, pp. 219-222.

Sakata, T. et al., "Direct transduction of allele-specific primer extension into electrical signal using genetic field effect transistor", *Biosensors and Bioelectronics*, vol. 22, 2007, pp. 1311-1316.

Sakata, T. et al., "DNA Analysis Chip Based on Field-Effect Transistors", *Japanese Journal of Applied Physics*, vol. 44(4B), 2005, pp. 2854-2859.

Sakata, T. et al., "DNA Sequencing Based on Intrinsic Molecular Charges", *Angewandte Chemie International Edition 2006*, vol. 118, 2006, pp. 2283-2286.

Sakata, T. et al., "DNA Sequencing Based on Intrinsic Molecular Charges", *Angewandte Chemie International Edition 2006*, vol. 45, 2006, pp. 2225-2228.

Sakata, T. et al., "DNA Sequencing Using Genetic Field Effect Transistor", *13th Intl. Conf. on Solid-State Sensors, Actuators and Microsystems*, Jun. 5-9, 2005, Seoul, Korea, 2005, pp. 1676-1679.

Sakata, T. et al., "Immobilization of oligonucleotide probes on Si3N4 surface and its application to genetic field effect transistor", *Materials Science and Engineering: C*, vol. 24, 2004, pp. 827-832.

Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.

Sakata, T. et al., "Potential Response of Genetic Field Effect Transistor to Charged Nanoparticle-DNA Conjugate", *Digest of Papers Microprocesses and Nanotechnology 2005, Tokyo, Japan*, 2005 Intl Microprocesses and Nanotech Conference, Hotel Bellclassic, 2005, pp. 42-43.

Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.

Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.

Sakata, T. et al., "Potentiometric Detection of DNA Using Genetic Transistor", *Denki Gakkai Kenkyukai Shiryo Chemical Sensor Kenkuykai*, CHS-03-51-55, 2003, pp. 1-5.

Sakata, T. et al., "Potentiometric Detection of Single Nucleotide Polymorphism by Using a Genetic Field-effect transistor", *ChemBioChem*, vol. 6, 2005, pp. 703-710.

Sakurai, T. et al., "Real-Time Monitoring of DNA Polymerase Reactions by a Micro ISFET pH Sensor", *Anal Chem*, vol. 64(17), 1992, pp. 1996-1997.

Salama, K., "CMOS luminescence detection lab-on-chip: modeling, design, and characterization", Thesis, Presented at Stanford University, 2005, pp. ii-78.

Salama, K., "Modeling and simulation of luminescence detection platforms", *Biosensors & Bioelectronics*, 2004, pp. 1377-1386.

Sawada, K. et al., "A novel fused sensor for photo- and ion-sensing", *Sensors Actuators B*, vol. 106, 2005, pp. 614-618.

Schasfoort, R. et al., "A new approach to immunoFET operation", *Biosensors & Bioelectronics*, vol. 5, 1990, pp. 103-124.

Schasfoort, R. et al., "Field-effect flow control for microfabricated fluidic networks", *Science*, vol. 286(5441), 1999, pp. 942-945.

Schoning, M. et al., "Bio FEDs (Field-Effect Devices): State-of-the-Art and New Directions", *Electroanalysis*, vol. 18(19-20), 2006, pp. 1893-1900.

SG200903992-6 Search and Examination Report Mailed Jan. 20, 2011.

Shah, N., "Microfabrication of a parellel-array DNA pyrosequencing chip", NNIN REU Research Accomplishments, 2005, pp. 130-131.

Shepherd, L. et al., "A biochemical translinear principle with weak inversion ISFETs", *IEEE Trans Circuits Syst—I*, vol. 52(12), Dec. 2005, pp. 2614-2619.

Shepherd, L. et al., "A novel voltage-clamped CMOS ISFET sensor interface", *IEEE*, 2007, pp. 3331-3334.

Shepherd, L. et al., "Towards direct biochemical analysis with weak inversion ISFETs", *Intl Workshop on Biomedical . . .*, 2004, S1.5-5-S1.5-8.

Shepherd, L. et al., "Weak inversion ISFETs for ultra-low power biochemical sensing and real-time analysis", *Sensors Actuators B*, vol. 107, 2005, pp. 468-473.

Shi, Y. et al., "Radical Capillary Array Electrophoresis Microplace and Scanner for High-Performance Nucleic Acid Analysis", *Anal. Chem.*, vol. 71(23), 1999, pp. 5354-5361.

Simonian, A. L. et al., "FET bases biosensors for the direct detection of organophosphate neurotoxins", *Electroanalysis*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenylnaphthalene Dimide as the Electrochemically Active Ligand", *Anal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

Truman, P., "Monitoring liquid transport and chemical composition in lab on . . . ", *Lab on a Chip*, vol. 6, 2006, pp. 1220-1228.

Uslu, F. et al., "Labelfree fully electronic nucleic acid detection system based on a field-effect transistor device", *Biosens & Bioelectron*, vol. 19(12), 2004, pp. 1723-1731.

Van Der Wouden, E. et al., "Directional flow induced by synchronized longitudinal and zeta-potential controlling AC-electrical fields", *Lab Chip*, vol. 6(10), 2006, pp. 1300-1305.

Van Hal, R.E.G. et al., "A general model to describe the electrostatic potential at electrolyte oxide interfaces", *Advances in Colloid and Interface Science*, vol. 69, 1996, pp. 31-62.

Van Kerkhof, J. et al., "The ISFET based heparin sensor with a monolayer of protamine as affinity ligand", *Biosensors & Bioelectronics*, vol. 10(3), 1995, pp. 269-282.

Van Kerkhof, J. et al., "ISFET Responses on a stepwise change in electrolyte concentration at constant pH", *Sensors Actuators B: Chemical*, vol. 18-19, 1994, pp. 56-59.

Van Kerkhof, J., "The Development of an ISFET-based Heparin Sensor", Thesis 1994.

Wagner, T et al., "'All-in-one' solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proc. of the Natl. Acad. of Sciences (PNAS)*, vol. 102(9), 2005, pp. 3208-3212.

Woias, P., "Modelling the short time response of ISFET sensors", *Sensors and Actuators B*, vol. 24-25, 1995, pp. 211-217.

Woias, P. et al., "Slow pH response effects of silicon nitride ISFET sensors", *Sensors and Actuators B*, vol. 48, 1998, pp. 501-504.

Wu, P. et al., "DNA and protein microarray printing on silicon nitride waveguide surfaces", *Biosensens Bioelectron*, vol. 21(7), 2006, pp. 1252-1263.

Xu, J-J et al., "Analytical Aspects of FET-Based Biosensors", *Frontiers in Bioscience*, vol. 10, 2005, pp. 420-430.

(56) References Cited

OTHER PUBLICATIONS

Yeow, T.C.W., "A very large integrated pH-ISFET sensor array chip compatible with standard CMOS processes", *Sensor and Actuators B*, vol. 44, 1997, pp. 434-440.

Yuqing, M. et al., "Ion sensitive field effect trnasducer-based biosensors", *Biotechnology Advances*, vol. 21, 2003, pp. 527-534.

Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.

Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.

METHOD AND SYSTEM FOR DELTA DOUBLE SAMPLING

RELATED APPLICATIONS

This application claims the benefit of U.S. Provisional patent application Ser. No. 61/386,403 filed on Sep. 24, 2010, the content of which is incorporated herein by reference in its entirety.

BACKGROUND

The presently disclosed embodiments deal with pixel arrays, and more particularly, to mismatch suppression and offset cancellation of components within the pixel arrays and readout circuits.

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as an "ISFET" (or pHFET). ISFETs conventionally have been explored, primarily in the academic and research community, to facilitate measurement of the hydrogen ion concentration of a solution (commonly denoted as "pH"). An ISFET is referred to, more generally, as a chemically-sensitive sensor herein.

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20 ("Bergveld"), which publication is hereby incorporated herein by reference in its entirety.

Details of fabricating an ISFET using a conventional CMOS (Complementary Metal Oxide Semiconductor) process may be found in Rothberg, et al., U.S. Patent Publication No. 2010/0301398, Rothberg, et al., U.S. Patent Publication No. 2010/0282617, and Rothberg et al, U.S. Patent Publication 2009/0026082; these patent publications are collectively referred to as "Rothberg", and are all incorporated herein by reference in their entirety. In addition to CMOS, however, biCMOS (i.e., bipolar and CMOS) processing may also be used, such as a process that would include a PMOS or NMOS FET array with bipolar structures on the periphery. Alternatively, other technologies may be employed wherein a sensing element can be made with a three-terminal devices in which a sensed ion leads to the development of a signal that controls one of the three terminals; such technologies may also include, for example, GaAs and carbon nanotube technologies.

Taking a CMOS example, a P-type ISFET fabrication is based on a P-type or N-type silicon substrate, in which an n-type well forming a transistor "body" is formed. Highly doped P-type (P+) regions S and D, constituting a source and a drain of the ISFET, are formed within the n-type well. A highly doped N-type (N+) region B may also be formed within the n-type well to provide a conductive body (or "bulk") connection to the n-type well. An oxide layer may be disposed above the source, drain and body connection regions, through which openings are made to provide electrical connections (via electrical conductors) to these regions. A polysilicon gate may be formed above the oxide layer at a location above a region of the N-type well, between the source and the drain. Because it is disposed between the polysilicon gate and the transistor body (i.e., the N-type well), the oxide layer often is referred to as the "gate oxide."

Taking another CMOS example, an N-type ISFET fabrication is based on a P+ wafer substrate with a P− epitaxy region of typically several microns thick, in which a P-type well creating a transistor "body" is formed. The P-type well is shared amongst all devices in the array and the P+ substrate serves as the bulk contact such that no other contacts are required at the pixel array. Highly doped N-type (N+) regions S and D, constituting a source and a drain of the ISFET, are formed within the P-type well. An oxide layer may be disposed above the source, drain and body connection regions, through which openings are made to provide electrical connections (via electrical conductors) to these regions. A polysilicon gate may be formed above the oxide layer at a location above a region of the N-type well, between the source and the drain. Because it is disposed between the polysilicon gate and the transistor body (i.e., the p-type well), the oxide layer often is referred to as the "gate oxide."

Like a MOSFET, the operation of an ISFET is based on the modulation of charge concentration (and thus channel conductance) caused by a MOS (Metal-Oxide-Semiconductor) capacitance. This capacitance is constituted by a polysilicon gate, a gate oxide and a region of the well (e.g., N-type well) between the source and the drain. When a negative voltage is applied across the gate and source regions, a channel is created at the interface of the region and the gate oxide by depleting this area of electrons. For an N-well, the channel would be a P-channel (and vice-versa). In the case of an N-well, the P-channel would extend between the source and the drain, and electric current is conducted through the P-channel when the gate-source potential is negative enough to attract holes from the source into the channel. The gate-source potential at which the channel begins to conduct current is referred to as the transistor's threshold voltage VTH (the transistor conducts when VGS has an absolute value greater than the threshold voltage VTH). The source is so named because it is the source of the charge carriers (holes for a P-channel) that flow through the channel; similarly, the drain is where the charge carriers leave the channel.

As described in Rothberg, an ISFET may be fabricated with a floating gate structure, formed by coupling a polysilicon gate to multiple metal layers disposed within one or more additional oxide layers disposed above the gate oxide. The floating gate structure is so named because it is electrically isolated from other conductors associated with the ISFET; namely, it is sandwiched between the gate oxide and a passivation layer that is disposed over a metal layer (e.g., top metal layer) of the floating gage.

As further described in Rothberg, the ISFET passivation layer constitutes an ion-sensitive membrane that gives rise to the ion-sensitivity of the device. The presence of analytes such as ions in an analyte solution (i.e., a solution containing analytes (including ions) of interest or being tested for the presence of analytes of interest), in contact with the passivation layer, particularly in a sensitive area that may lie above the floating gate structure, alters the electrical characteristics of the ISFET so as to modulate a current flowing through the channel between the source and the drain of the ISFET. The passivation layer may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in an analyte solution, whereas passivation layers comprising polyvinyl chloride containing valinomycin provide sensitivity to potassium ion concentration in an analyte solution. Materials suitable for passivation layers and sensitive to other ions such as sodium, silver, iron, bromine, iodine, calcium, and nitrate, for example, are known, and passivation layers may comprise various materials (e.g., metal oxides, metal nitrides, metal oxynitrides). Regarding the chemical reactions at the analyte solution/passivation layer interface, the surface of a given material employed for the passivation layer of the ISFET may include chemical groups that may donate protons to or accept protons from the analyte solution, leaving at any given time negatively charged, positively charged, and neutral sites on the surface of the passivation layer at the interface with the analyte solution.

With respect to ion sensitivity, an electricstatic potential difference, commonly referred to as a "surface potential," arises at the solid/liquid interface of the passivation layer and the analyte solution as a function of the ion concentration in the sensitive area due to a chemical reaction (e.g., usually involving the dissociation of oxide surface groups by the ions in the analyte solution in proximity to the sensitive area). This surface potential in turn affects the threshold voltage of the ISFET; thus, it is the threshold voltage of the ISFET that varies with changes in ion concentration in the analyte solution in proximity to the sensitive area. As described in Rothberg, since the threshold voltage VTH of the ISFET is sensitive to ion concentration, the source voltage VS provides a signal that is directly related to the ion concentration in the analyte solution in proximity to the sensitive area of the ISFET.

Arrays of chemically-sensitive FETs ("chemFETs"), or more specifically ISFETs, may be used for monitoring reactions—including, for example, nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Such use of ChemFET (or ISFET) arrays involves detection of analytes in solution and/or detection of change in charge bound to the chemFET surface (e.g. ISFET passivation layer).

Research concerning ISFET array fabrication is reported in the publications "A large transistor-based sensor array chip for direct extracellular imaging," M. J. Milgrew, M. O. Riehle, and D. R. S. Cumming, Sensors and Actuators, B: Chemical, 111-112, (2005), pp. 347-353, and "The development of scalable sensor arrays using standard CMOS technology," M. J. Milgrew, P. A. Hammond, and D. R. S. Cumming, Sensors and Actuators, B: Chemical, 103, (2004), pp. 37-42, which publications are incorporated herein by reference and collectively referred to hereafter as "Milgrew et al." Descriptions of fabricating and using ChemFET or ISFET arrays for chemical detection, including detection of ions in connection with DNA sequencing, are contained in Rothberg. More specifically, Rothberg describes using a chemFET array (in particular ISFETs) for sequencing a nucleic acid involving incorporating known nucleotides into a plurality of identical nucleic acids in a reaction chamber in contact with or capacitively coupled to chemFET, wherein the nucleic acids are bound to a single bead in the reaction chamber, and detecting a signal at the chemFET, wherein detection of the signal indicates release of one or more hydrogen ions resulting from incorporation of the known nucleotide triphosphate into the synthesized nucleic acid.

A problem that exists within many of these circuits and arrays relates to tolerances in the circuit fabrication process. The same types of circuits may have somewhat different characteristics from one another because of inherent variances in the circuit components and their relative structures that occur from fabrication tolerances. These differences in circuits that are intended to be identical circuits is often referred to as a mismatch.

An example of offset and mismatch may be an amplifier mismatch that occurs in circuits due to threshold mismatch between the devices of the input differential pair that are intended to be identical. Arrays having numerous amplifiers that are intended to be identical, but are not, are typical of circuits that can exhibit mismatch. Active pixel sensors are an example of devices where this mismatch and offset may be critical. Active pixel sensors are image sensing arrays having a number of pixels, and each pixel is associated with an amplifier to output the light sensed by that pixel. A common approach to correcting for amplifier mismatch within active pixel sensors is correlated double sampling. In correlated double sampling, one sample is taken of a reset pixel value and another sample taken of the pixel with the signal from sensed light. A difference is taken between the two samples. The difference in samples should represent the actual signal free of offsets including a reduction in thermal noise if the samples are time correlated. In order to acquire the two samples, a reset value is required. Correlated double sampling can be effective in removing various types of offsets and transistor mismatch problems.

However, there are sensing arrays that have sensing elements that are continually being read over a time period may not enable reset circuits to be used within those sensing elements. Without this reset value to be sampled, correlated double sampling is not a useable technique because of the absence of a reset value or reference value that is correlated to the sensing devices. Therefore, there is a need in the prior art for providing double sampling circuits that cannot employ correlated double sampling techniques.

In addition, transistor mismatch in CMOS circuits can impose severe limitations for sensor arrays. This may be especially true for sensors with small output levels. The total deviation that inherently results during the fabrication processes creates non-uniformity in the transistors within the array of sensors resulting in signal offsets and non-uniformity within the signal created by these transistors. Therefore, it is desirable to eliminate or reduce such non-uniformity and offsets, especially before the A/D conversion. From the foregoing discussion, there remains a need within the art for a circuit that can eliminate offsets and mismatches within circuits, even those without reset capabilities.

DETAILED DESCRIPTION

Embodiments may be discussed herein that apply sampling techniques that do not require reset circuits in order to function properly. In an embodiment, a method to attenuate circuit component offsets and mismatches may be provided. A pixel output may be precharged to a first bias level. The pixel may include a chemically-sensitive sensor and a select transistor that are a matched pair of transistors. A a reference signal sample from the select transistor in the pixel may be sampled. Offset and mismatch signal artifacts from the reference sample may be canceled to leave an offset and mismatch correction signal at a circuit node. A selected input signal from the chemically-sensitive sensor in the pixel is sampled. The sampled input signal may be adjusted according to the offset and mismatch correction signal at the circuit node. The adjusted sampled input signal may be converted from an analog signal to a digital signal.

Another embodiment provides system for performing delta double sampling. The system includes a pixel having a chemically-sensitive sensor for providing an input signal in response to a chemical reaction, and a select transistor for providing a reference sample. The system may also included a sampling circuit, a comparator circuit and a latch. The sampling circuit may be configured to take the reference sample from the select transistor and an input signal sample from the chemically-sensitive sensor through the select transistor. The comparator circuit may output a first comparison result of the reference sample to a reference voltage and to perform analog-to-digital conversion by outputting a second comparison result that includes a signal indicating a value of the input signal sample in comparison to a digital threshold reference signal. The latch may provide a control signal to the sampling circuit in response to the first comparison result and output a digital signal value in response to the second comparison result.

Another embodiment provides for a system including a single transistor chemically-sensitive pixel and a characterization transistor. The single transistor chemically-sensitive pixel may provide an input signal in response to a chemical reaction. The characterization transistor may provide a reference sample, wherein the characterization transistor is outside the pixel.

Figure 1:
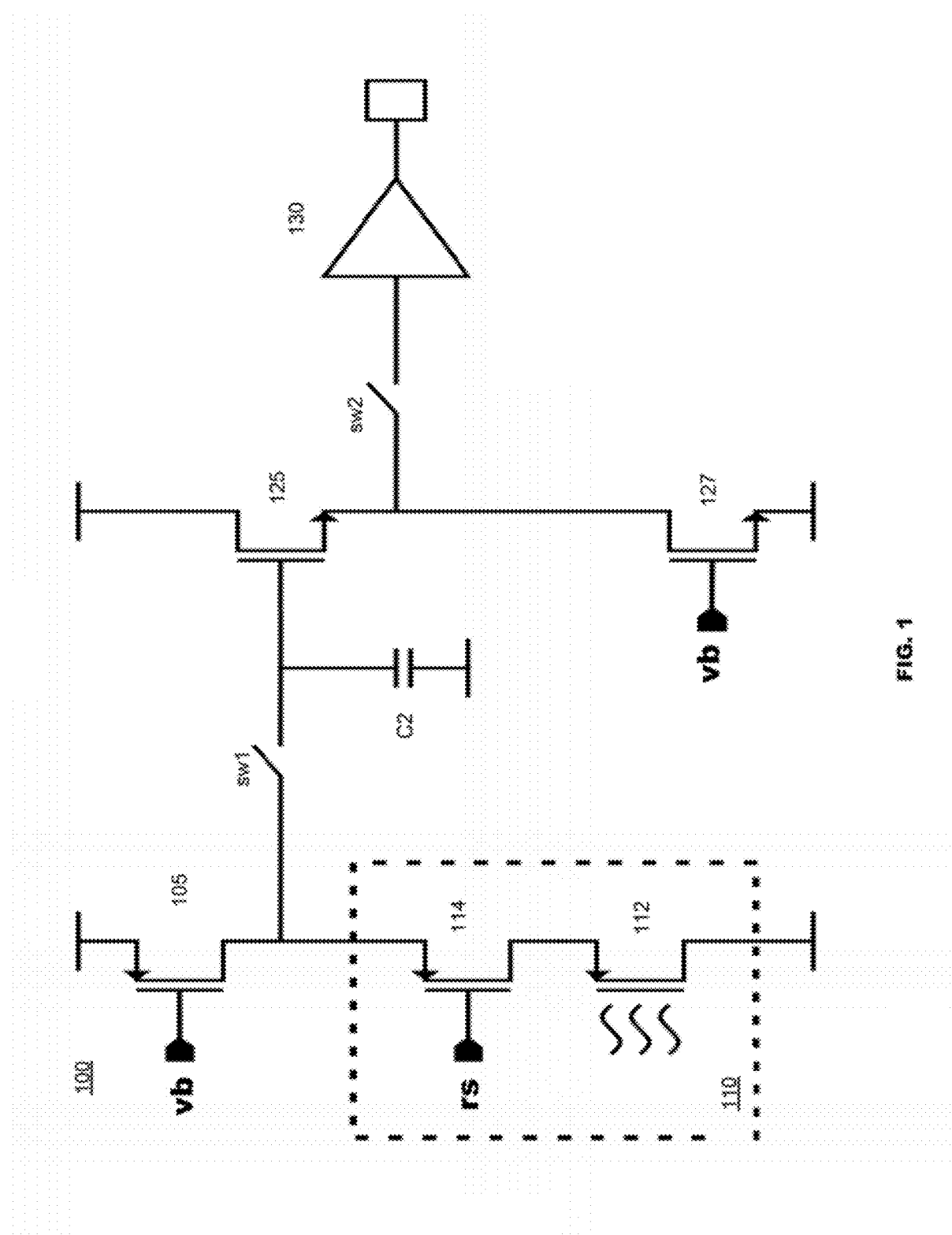
FIG. 1 is an exemplary circuit that may exhibit transistor mismatch.

FIG. 1 is an example of a circuit exhibiting transistor and amplifier mismatch. The circuit 100 may have offsets and mismatches in pixel 110, transistors 105, 125, 127, and buffer 130 may combine to create signal non-uniformity. The pixel 110 may be a two transistor 112 and 114 pixel that does not have a reset function. One of the transistors 112 may be a chemically-sensitive sensor that detects a small signal resulting from a chemical reaction that generates a signal as a result. An analog to digital converter (ADC) (not shown) may be connected to the output of buffer 130 to convert the analog output signal to a digital signal. However, if the analog output signal is non-uniform, the ADC, in order to accurately resolve the analog output signal to a digital signal, will require additional bits allocated over a wide dynamic range—the more non-uniform the output signal from buffer 130, the more bits will be required. In addition, if the amplitude of the desired signal contained on the signal output from the output of buffer 130 is small compared to the entire output signal, the greater the effect signal non-uniformity has on the overall signal, which results in an inefficient allocation of bits. The offsets and mismatches, therefore, impose higher bit-depth requirements. In an embodiment, the required dynamic range of an off-chip ADC may be, for example, approximately 250 mV. This dynamic range may provide for large signal sizes and a high degree of resolution. As an example, a small signal that is contained on a signal that is large in amplitude due to a non-uniform nature of the signal may have requirements to reach a quantization noise level of 10 uV, and require a 12-14 bit resolution for an ADC in order to be accurately resolved.

Figure 2:
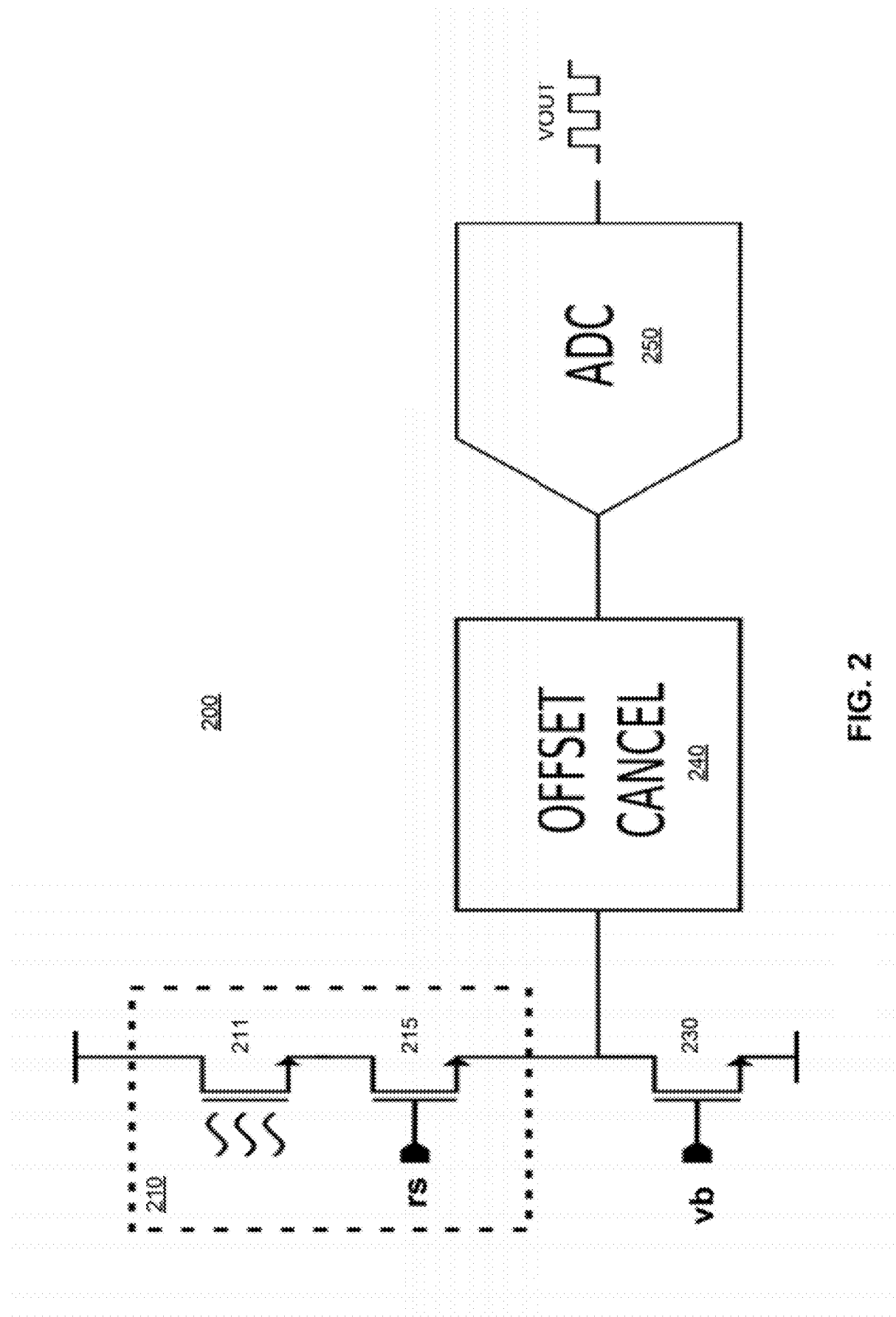
FIG. 2 is an exemplary block diagram incorporating components according to an embodiment of the present invention.

FIG. 2 illustrates an exemplary block diagram incorporating components according to an embodiment of the present invention. The system 200 may include a pixel 210, a bias transistor 230, an offset cancel block 240, and an analog-to-digital converter 250. The pixel 210 may include a matched pair of transistors: a chemically-sensitive sensor 211 and a row select transistor 215, where matched transistors means that the transistors 211 and 215 are both similar size, shape and type. To qualify as matched pair, not all properties of the devices need be identical. For example, both transistors may have the same width and share the same diffusion region but have nominally different gate lengths. Since the devices are minimally spaced apart, their gate oxide regions will be well matched. This causes the threshold of the devices to be well matched in comparison to devices that are further separated. Devices with different gate lengths will produce a measured difference in output levels but all matched pairs will be behave in the same systematic way and preserve uniformity. One difference may be that the chemically-sensitive sensor 211 may differ from row select transistor 215 by having a chemically-sensitive well coupled to a floating gate that provides an input signal. Other differences may exist as long as the differences are systematic and remain consistent between the matched pairs.

Generally, transistors formed close together have less mismatch. The benefit of using matched transistors 211 and 215 in the same pixel is that, because the row select transistor is adjacent to the chemically-sensitive sensor, it will have less transistor mismatch. Thus a reference level may be taken from the row select transistor in the same pixel as the chemically-sensitive sensor as an approximate matching reference for the sensor transistor.

However, all of the components in the pixel 210 and bias transistor 230 may have some form of offsets and mismatches that may contribute to output signal non-uniformity. The combined offset and mismatch in pixel 210 and bias transistor 230 may be sampled into the offset cancel block 240 and removed before analog-to-digital conversion by the ADC 250. When the input signal range is small, dynamic range requirements of the ADC 250 may drop to, for example, an 8-bit level since only the actual signal level is converted. In general, the transistor mismatch is removed or reduced and the sensor response is made uniform.

A method of addressing the mismatch will be explained with reference to FIG. 2. The biasing transistor 230, which may be a FET, may function to bias the pixel 210 through a bias voltage vb at the gate of biasing transistor 230. The ADC 250 provides a digital output for the signal from pixel 210. Offset Cancel 240 may be a column level circuit that provides double sampling capabilities to analyze pixel 210. The offset functions of the Offset Cancel 240 may eliminate the combined offsets and mismatches within pixel 210, biasing transistor 230 and any other components in the signal path. The Offset Cancel 240 may receive a first sample of the entire signal path absent the sensed signal on chemically-sensitive sensor 211. The first sample may include the combined offsets and mismatches of all the components, for example, chemically-sensitive sensor 211 and transistor 215 of pixel 210 and biasing transistor 230, in the entire signal path. A second sample of the signal path may be taken with the sensed signal value from the chemically-sensitive sensor 211 included in the sampled value. The second sample of the entire signal path may include the combined offsets and mismatches of all the components, for example, chemically-sensitive sensor 211 and transistor 215 of pixel 210 and biasing transistor 230, in the entire signal path as well as the sensed signal value of chemically-sensitive sensor 211. Offset Cancel 240 may provide a difference function that subtracts the first sample from the second sample including the sensed signal value from the chemically-sensitive sensor 21, which leaves the sensed signal value to be provided to the ADC 250. In summary, the Offset Cancel 240 may take the two samples, may employ a double sampling technique on the two samples, and may remove offsets and mismatches of pixel 210, and biasing transistor 230 using the two samples before analog to digital conversion by ADC 250. The dynamic range requirement of ADC 250 may be reduced since only the actual sensed, signal-level of chemically-sensitive sensor is converted. In a specific embodiment, the bit length drops to an 8-bit level since only the actual signal level is converted. As a result, circuit component mismatch is removed/reduced and sensor response is made uniform.

Figure 3A:
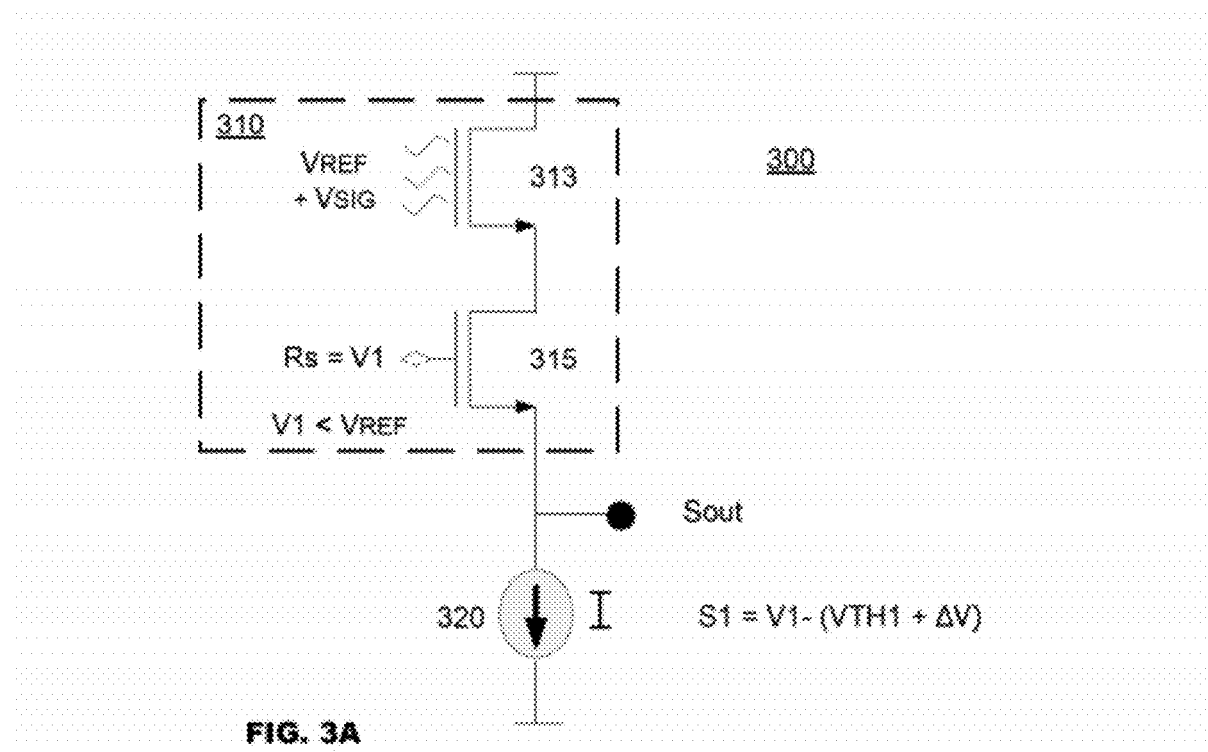
FIG. 3 is an example of a matched transistor pair used for sampling according to an embodiment of the present invention.
Figure 3B:
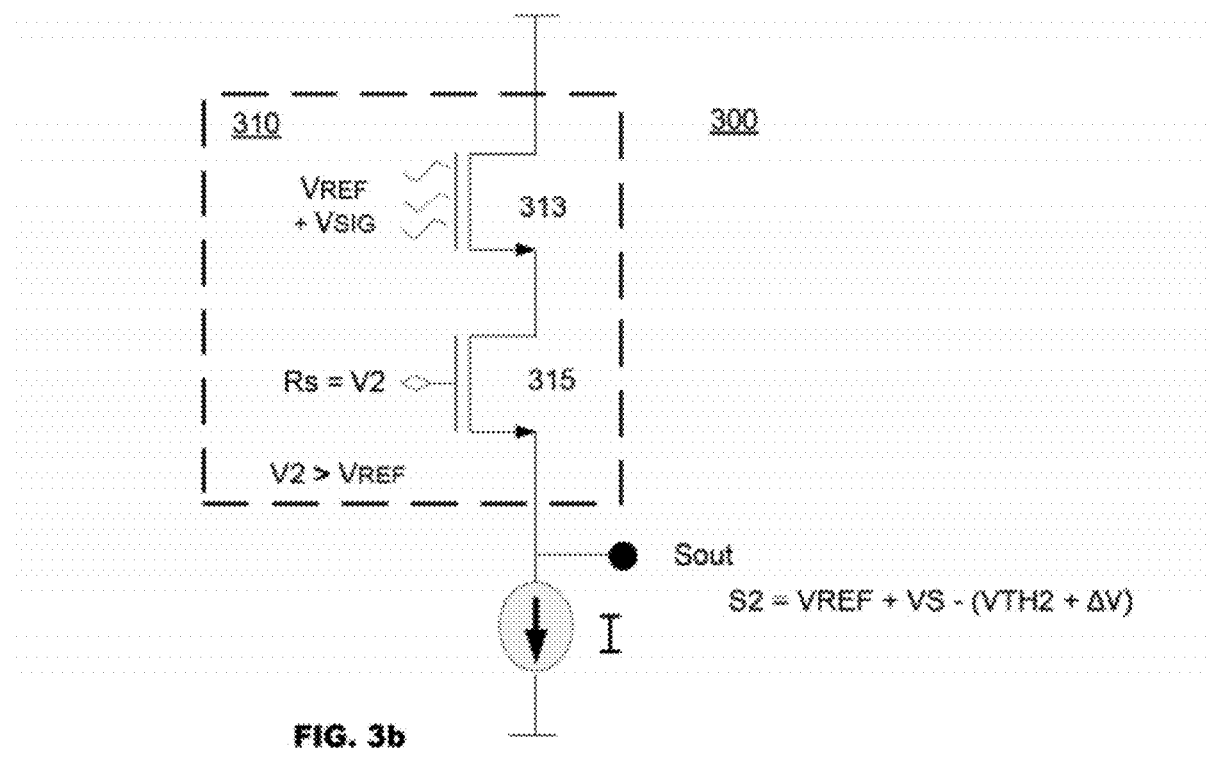

FIGS. 3A and 3B illustrate an example of delta double sampling using the matched pair of transistors according to an embodiment of the present invention. In the circuit 300 of FIG. 3A, the pixel 310 may be biased by a current source I (e.g., a transistor such as transistor 230 of FIG. 2). The pixel 310 may include a chemically-sensitive sensor 313, and a row select transistor 315, both of which may be a FET. For clarity, the matched pair includes chemically-sensitive sensor 313 and row select transistor 315. These devices are considered a matched pair due to their close proximity and the properties in the example of FIG. 2. The pixel 310 may be one of a plurality of pixels that are used within an array (not shown) that is arranged in rows and columns. Select transistor 315 may be controlled by a row select signal rs that is used to select the pixel 310. In a correlated double sampling algorithm, a signal sample may be taken of the device in two different states. A sample may be taken of the pixel 310 in a first state without an input signal (known or unknown, or in a reset mode), so any offsets or mismatches of the device may be characterized, and another sample may taken of the pixel 310 in a second state of the device that typically includes the input signal. The difference between the two samples is considered a representation of the input signal without the presence of the pixel 310 offsets (e.g., transistor fabrication differences such as voltage threshold differences). However, in the present embodiment, the chemically-sensitive sensor 313 may be read out continuously while the reaction being monitored is occurring. Accordingly, there is no opportunity to take a sample without an input signal or a known input signal from the chemically-sensitive sensor 313.

In an example, the reaction being monitored and read out continuously as it occurs may be a hydrogen ion (H+) released during a DNA sequencing event that occurs when a nucleotide is incorporated into a strand of DNA by a polymerase. As each nucleotide incorporates, a hydrogen ion (H+) is released. Since the chemically-sensitive sensor 313 is being read continuously during the period of time the incorporation signal is being generated, the chemically-sensitive sensor 313 cannot be reset, which eliminates the possibility of using correlated double sampling to remove and attenuate offsets. Since the actual chemically-sensitive sensor 313 cannot be measured without its input signal, the actual chemically-sensitive sensor 313 is replaced by its nearest neighbor, the row select transistor 315 to establish the correlation. The row select transistor 315 may provide the closest approximation of the offset and mismatch characteristics of the chemically-sensitive sensor 313 since it is locally matched to the chemically-sensitive sensor 313. The row select transistor 315 may likely share common mismatches and offsets with the chemically-sensitive sensor 313 since the row select transistor 315 is fabricated with, and is in close proximity to the chemically-sensitive sensor 313. As shown in FIG. 3A, the row select transistor 315 can be biased by a voltage V1 such that it operates in the saturation region to establish a local threshold voltage correlation (VTH1). Essentially, the row select transistor 315 hides the input signal when it is forced into saturation. The voltage V1 is also less than VREF, which may be the effective DC bias level of the sensor electrode as it appears at the gate of the sensor transistor 313. An exemplary voltage for V1 may be approximately 1.5V and an exemplary voltage for VREF may be approximately 2.5V. This local threshold voltage correlation (VTH1) may be used to perform (delta) double sampling. By keeping the row select transistor 315 in saturation mode, negligible signal or noise at the sensor transistor 313 may pass through the row select transistor 315 during the first reference sample. The first signal sample, i.e., reference sample, S1 is a characterization of the row select transistor 315, which is an accurate substitute for the chemically-sensitive sensor 313 due to their proximity to one another. The first signal sample S1 may be equal to V1−(VTH1+ΔV), where ΔV is the overdrive voltage for biasing the transistor at the given bias current level. This value may remain constant within a pixel but may vary between pixels and largely from column to column due to bias current mismatches in the column-level bias circuitry. The first sample S1 may be output from the circuit 300 at output Sout. FIG. 3B illustrates the taking of the second signal sample S2.

In FIG. 3B, the row select transistor 315 can be biased by a voltage V2 such that it operates in the triode region to establish a local threshold voltage correlation of the transistor 313 (VTH2). The voltage V2 is greater than VREF, which may be an effective supply voltage. VREF may be a constant bias voltage that does not change between the reference sample and the signal sample. This local threshold voltage correlation (VTH2) may be used to perform (delta) double sampling. By keeping the row select transistor 315 in the triode region, the ion signal (H+) from the chemically-sensitive sensor 313 may pass through the row select transistor 315 during the second signal sample. The chemically-sensitive sensor 313 may operation in the transistor saturation region. The second signal sample S2 may include the input signal VSig and VREF from the chemically-sensitive sensor 313. The second signal sample S2 may equal VREF+VSig−(VTH2+ΔV),. The second sample S2 may also be output from the circuit 300 at output Sout.

A differencing function may produce the result of S2-S1 as approximately equal to VSig+(VREF-V1)+(VTH1-VTH2), note that the constant voltages ΔV cancel. The voltage (VREF−V1) may be a constant voltage set to an ADC reference voltage, in which case, the ADC may effectively remove the (VREF−V1) term. The threshold voltages VTH1 and VTH2 may be substantially equal or the difference may be a systematic constant resulting from the matched pair configuration. Therefore, the resulting residue from (VTH1-VTH2) may be minimal and consistent across the array of pixels. Any constant residue in this difference term may be absorbed in the ADC reference. More specifically, this difference term is zero when the transistors are of equal size. When the transistors are not of equal size or dissimilar in any other way, the resulting residue may simply be added together with the other constant terms that establish the ADC reference. This leaves the signal voltage VSig without any pixel offset artifacts to be applied to the ADC. Depending upon where in the signal path the samples are collected, additional signal offset artifacts may be collected in the first sample and be attenuated during the differencing function of the delta double sampling operation. This allows for double sampling the entire signal chain before the ADC. Portions of the ADC may also become part of the offset cancellation scheme as well. For example, if the ADC has an input stage that is subject to offsets, these offsets may be cancelled as part of the two samples without requiring two separate data conversions. Of course, the order of the sampling may differ. In addition, the voltages V1 and V2 may be programmable, and may switch on between row selection of the respective pixel during readout and the cascode level. In an alternative embodiment, the double sampling algorithm can also be applied after the ADC, whereby the ADC performs two data conversion cycles and the difference between the samples is performed in digital logic. The digital logic may be implemented as hardware on-chip or by software or hardware off-chip. This may be considered digital delta double sampling. This has advantages where multiple ADCs convert columns of pixel readouts simultaneously and where the ADCs have inherent offsets. Further, double delta double sampling may be performed by applying the differencing functions both before the ADC and after the ADC. The first differencing function may establishe a largely uniform signal for input into the ADC, thereby reducing the required dynamic range of the ADC. The second differencing function may be placed after the ADC to cancel the offsets in the ADCs. The first and second differencing functions produce complete offset cancellation of all circuit components. With this approach, second order effects, which are due to non-idealities in transfer functions of the underlying circuitry can be reduced since uniformity is maintained at all points in the signal chain.

The above described matched-pair delta double sampling (MPDDS) works by sampling the full signal path, first without the input signal and then second with the input signal. By subtracting the two samples before the A/D conversion, only the difference (delta) between the samples is converted. This difference in samples represents the actual signal free from non-uniformity. Because the signal level is small compared to the offsets that are removed in the process of MPDDS, significant savings in the resolution (bit-depth) of the ADC is achieved. In addition, subsequent processing to clean up any non-uniformity between samples is reduced. By way of example, the offsets in a typical signal chain may be as large as 200 mV, while the signal range is within a 1 mV range. Without offset cancellation, it is necessary to establish a dynamic range of at least 200 mV even though the signal range is 1 mV. With offset cancellation, assuming that the non-uniformity is reduced to within the range of the signal level, the dynamic range may be reduced to 2 mV. This represents a 100 fold reduction in the dynamic range of the ADC (approximately 7 bits of reduction) in this example.

Figure 4:
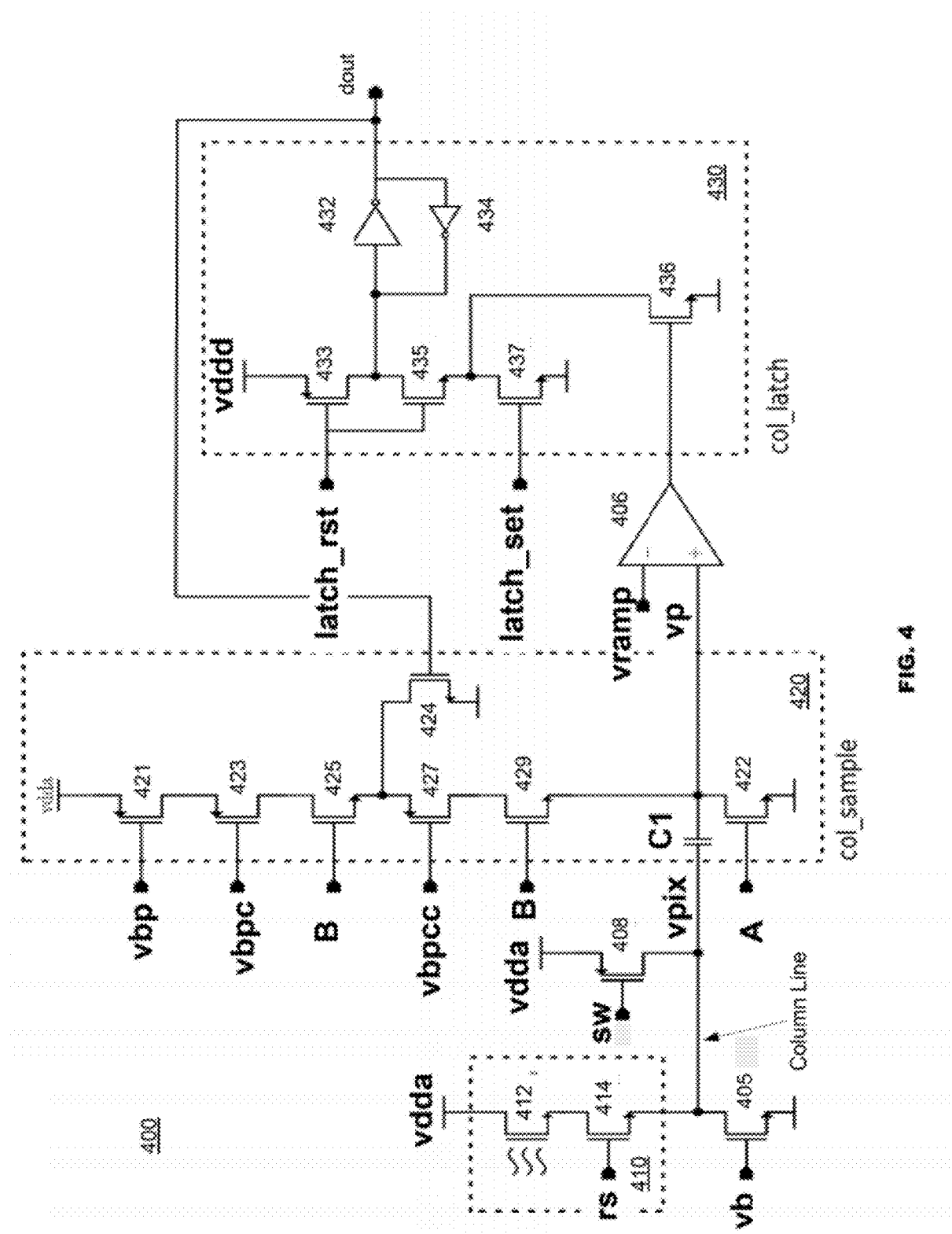
FIG. 4 is an example of a sampling circuit using a matched transistor pair for sampling according to an embodiment of the present invention.

FIG. 4 illustrates a system according to an embodiment of the present invention. The system 400 may include four circuit blocks: a pixel 410, column sample circuit 420, a comparator 406, and a column latch 430. Biasing transistor 405 may bias pixel 410 based on bias signal vb. Transistor 408 may provide a precharge signal based on the control input sw. This transistor 408 can be of either type depending on whether the column is precharged to the supply voltage, the substrate voltage or some other reference voltage in between the supply and substrate voltages. The pixel 410 may be a two transistor design with a row select transistor 414 connected to the source of a chemically-sensitive sensor 412. The drain of the chemically-sensitive sensor 412 may be coupled to a supply voltage Vdda. In practice, this can be a column line that is switched to the Vdda supply voltage. The source of the row select transistor 414 may output from the pixel 410 and couple to column sample circuit 420 and the biasing transistor 405. The column sample 420 may provide a readout circuit for reading out pixels 410. The column sample 420 may include a double cascoded current source including transistors 421, 423, and 427 (which form a current source) and transistors 425 and 420 (which form switches to enable the current source), a sampling capacitor C1, a reset transistor 422, and current steering transistor 424. The input signals Vbp, Vbpc and Vbpcc provide respective bias signals to bias the current provided by the respective transistors 421, 423, and 427. The comparator 406 may provide a comparison function for an input received from the column sample circuit 420 and a reference voltage Vramp. The comparator 406 may have inverting and non-inverting inputs, control inputs and an output, and may be a high gain amplifier with a low input-referred noise level. The bandwidth of the comparator 406 may be controlled by internal or external control signals (not shown) from a control circuit to vary the bandwidth of the comparator, such that the comparator's bandwidth can be changed from one phase to another depending upon the function that is desired from the comparator 406. The comparator 406 may be connected to the column latch 430. The column latch 430 may be an SR-latch. The latch 430 may be reset with 'latch_rst' and set with either 'latch_set' or the output of the comparator. The output of the latch circuit 430 may feed back to the column sample 420.

In operation, the comparator 406 and column latch circuit 430 may be used for offset cancellation during the first sample phase and then later used for the A/D conversion in the second phase. Therefore, the only additional circuitry needed for the MPDDS system 400 may be a sampling capacitor and a few transistors. The sampling capacitor C1 may be made smaller than the required KTC noise level by keeping the bandwidth of the comparator 406 larger than the bandwidth of the current source mirror fashioned by transistors 421, 423 and 427. The reduction in KTC noise achieved in the sampling capacitor is known to those skilled in the art. Here, the KTC noise reduction is being used with delta double sampling to achieve offset cancellation with a small layout footprint. Since the comparator is used during the capture of the first sample and then during the ADC cycle which converts the second sample minus the first sample, the comparator offset, and hence the offset of the ADC is largely removed. Therefore, the offset cancellation circuitry and the ADC are largely integrated together as one unit, while still performing separate operations.

Figure 5:
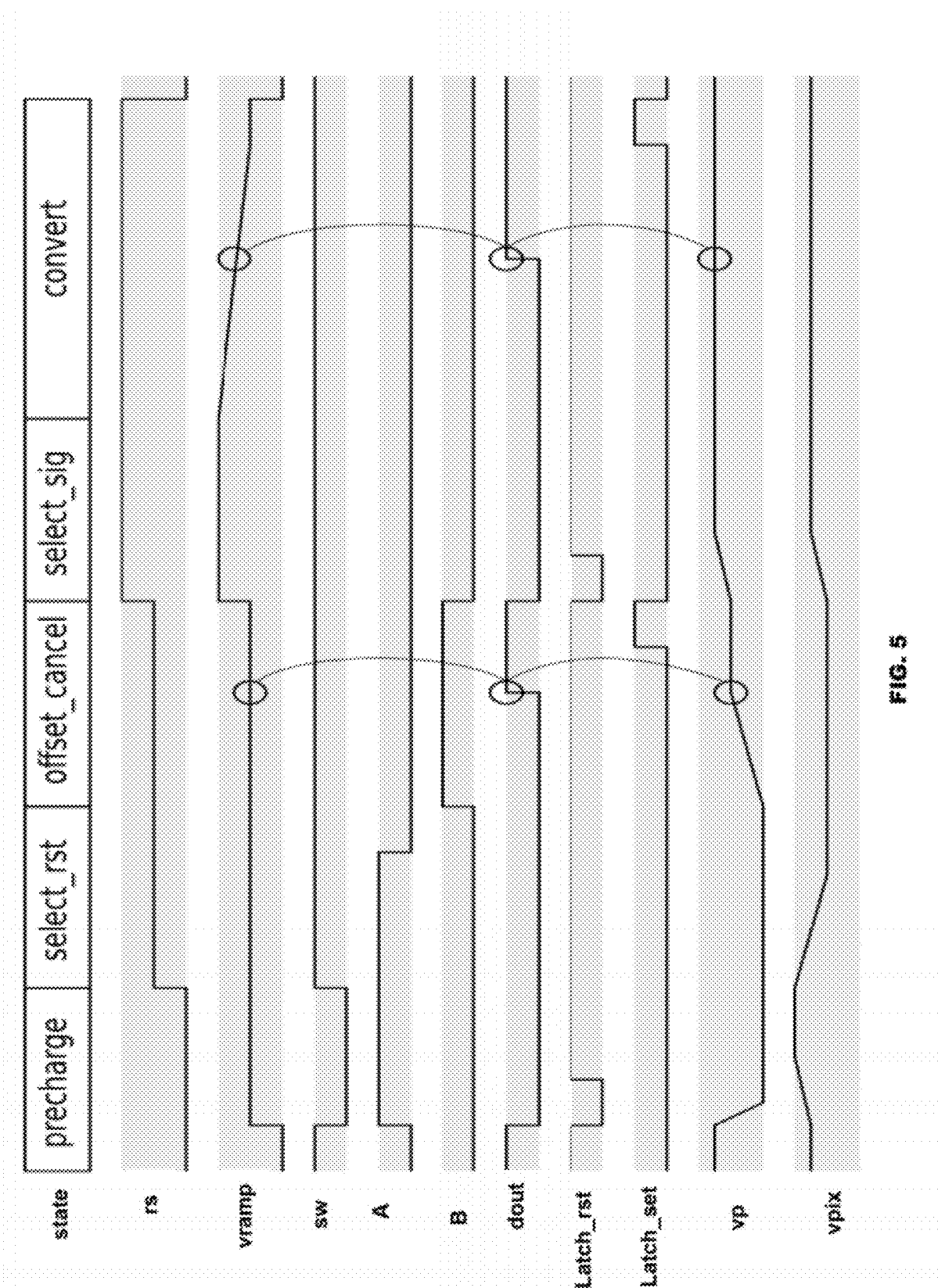
FIG. 5 is an exemplary timing diagram for operation the sampling circuit of FIG. 4 according to an embodiment of the present invention.

FIG. 5 illustrates the timing of operation of the MPDDS system 400 of FIG. 4. The timing of the MPDDS system 400 may categorized into five phases of operation as shown in FIG. 5: a precharge phase, a row select (select_rst) phase; an offset cancel phase; select signal phase and convert phase.

During the precharge phase, the pixel 410 column line may be switched to a constant bias level such as analog ground.

The col_latch 430 may be reset by switching 'latch_rst' low. At the same time, the sampling capacitor C1 terminal at transistor 422 may be switched to ground and held low throughout the subsequent row select phase. During the precharge phase, initial biasing conditions are established. No rows are selected during this phase so the pixel column line, represented by vpix, is driven to the initial biasing conditions. When using MOS transistors with a negative threshold voltage, the level of precharge may be set to a level higher than ground in order to effectively turn off the unselected pixels.

During the row select phase, the 'rs' line may be switched to a mid-level voltage (for example 1.5V) that causes the row select device 414 to enter saturation and charge the column line. The reference voltage on the chemically-sensitive sensor 412 may be at a higher level than the 'rs' line during this phase (for example 2.5V). This ensures that the row select device 414 stays in saturation. During the row select phase, the value of the column line may be driven to the voltage of the gate of the row select device 414 less the threshold voltage and the gate to source overdrive voltage required for a given bias current. Because the gate of the row select device 414 is held at a lower voltage than the gate of the chemically-sensitive sensor 412, the row select device 414 operates in the saturation region and does not behave like a switch. Since the output resistance of the drain of row select device 414 is very high, the signal and noise at the source of chemically-sensitive sensor 412 cannot modulate the source of row select device 414. This blocks the signal and noise at the input of the pixel during the offset cancel phase. Therefore, instead of resetting the pixel 410 to obtain the correlation value, the signal from the data path is blocked by forcing row select device 414 into saturation. Details of the biasing conditions and equations were discussed above with respect to FIGS. 3A and 3B.

When entering the offset cancel phase, line 'A' is turned off and line 'B' is turned on. This causes the 'vp' terminal at the comparator 406 to start charging. When the 'vp' terminal terminal rises above the 'vramp' level, the comparator 406 may fire, which shuts off the current source 436 and establishes the first sample level. Since the comparator 406 has a higher bandwidth than the charging circuit that forms the current source, the thermal noise voltage at the capacitor C1 is reduced to less than sqrt(KT/C). The offset for the signal chain is now stored in the sampling capacitor C1. Next, both lines 'A' and 'B' are turned off, and the latch 430 is reset again while the vramp line to the comparator 406 is increased to its maximum level, which may exceed the effectively output level of the bias and signal level at the chemically-sensitive sensor 412. The offset cancel period may contain timing sequences which effectively emulate a negative feedback loop which servos the voltage of the capacitor C1 to the value needed to match the reference voltage at the comparator set by the Vramp input. The goal is to charge the sampling capacitor C1 to a value that causes the comparator 406 to fire for the given reference at the Vramp input to the comparator 406. Because the comparator 406 and the data path to the comparator 406 remain unchanged from the row select period to the signal select period, the comparator 406 will always fire when the same differential voltage is applied. Therefore, the first sample onto the comparator 406 effectively "characterizes" the data path and stores the value needed to zero out the comparator and data path. The vp node initially starts at a voltage established during the precharge period such as ground. The vp voltage may be initialized to a voltage lower than the vramp reference voltage including the magnitude of the total mismatch between all comparators 406. When the A line is released, and the B line is activated and a current source (such the current source formed from transistors 421, 423 and 427) starts charging the capacitor C1. In essence, the input (vramp) to the comparator 406 is being swept by the vp input until the comparator 406 fires. Once the comparator 406 fires, the current source is turned off and the value that is required to fire the comparator 406 is locked into the capacitor C1. Now that this value is locked into the capacitor C1, any new input levels presented on the vpix line (i.e., column line) will only be represented to the comparator 406 as the difference (delta) between the new value and the initial value. Therefore, the subtraction between the samples is inherent in the configuration. The bandwidth of the comparator 406 in this phase may be controlled to be at a certain, first bandwidth to provide fast operation and KTC noise suppression.

During the select signal phase, the 'rs' line is switched to its highest potential, which pushes the row select device 414 into triode region. The signal level at the chemically-sensitive sensor 412 is now presented on the column line attached to the sampling capacitor C1. The chemically-sensitive sensor 412 voltage is then coupled through the sampling capacitor C1 and held while the vramp voltage falls.

During the conversion phase (or the select signal phase), a gray code count may be distributed to all the columns. When the comparator 406 fires, 'dout' goes high and latches in the gray code count (not shown), which represents the digital value of the pixel 410. The ramp line (i.e. Vramp) may be set to a voltage which always exceeds the new vpix voltage. To start the A/D conversion, the vramp line may decrease in voltage in synchronization with the gray code counter. When the ramp value (Vramp) causes the comparator 406 to fire, the corresponding gray code gets latched into local registers corresponding to that column line. The latched gray code then represents the offset cancelled signal. The bandwidth of the comparator 406 in the later conversion phase may be controlled to be at a second bandwidth to provide slower operation compared to the earlier offset cancellation phase. By operating slower, the comparator may provide filtering of thermal fluidic noise generated by the system.

The offset cancel phase has been described with a comparator 406, latch 430 and a current source within column sample 420 to charge the sampling capacitor C1. Alternatively, it is possible to use a continuous-time feedback and treat the comparator 406 as an operational amplifier. In this case, the output of the amplifier is switched onto the inverting input terminal of the amplifier. The high gain in the comparator 406 forces the input terminals to become substantially equal. In this way, the offset of the comparator 406 and the offsets before the capacitor C1 are sampled and cancelled when the amplifier operates in the open loop configuration during the conversion phase. In this case, the continuous time negative feedback loop performs the required offset cancellation. The method described using the column latch configuration can make use of a smaller capacitor than the continuous time implementation because the thermal noise from sampling can be reduced with the proper allocation of bandwidths. The comparator may have larger bandwidth than the current source charging circuit. In order to achieve this larger bandwidth, the output resistance of the charging circuit may be kept to a high level by using multiple cascode devices.

Figure 6:
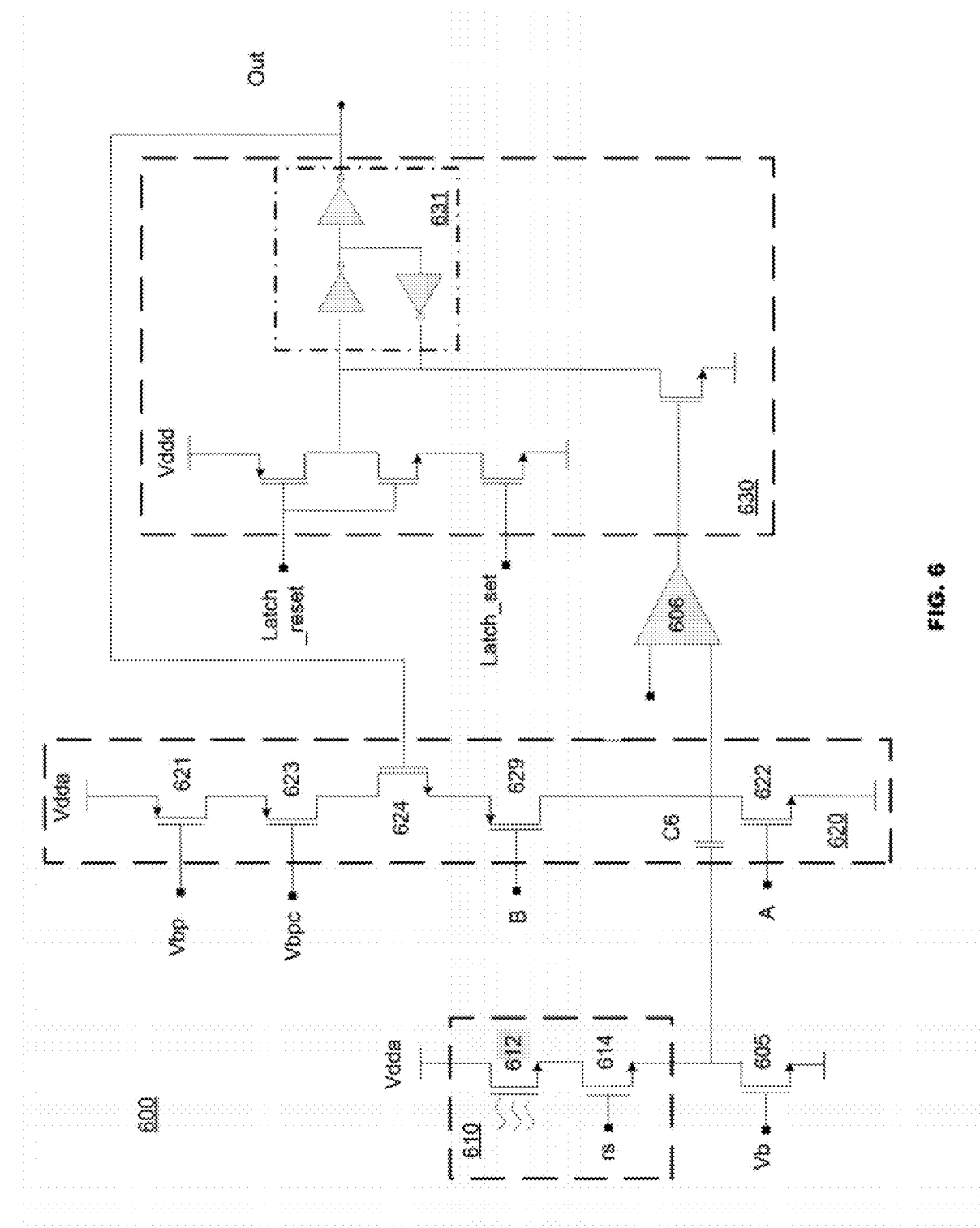
FIG. 6 illustrates another example of a sampling circuit using a matched transistor pair for sampling according to an embodiment of the present invention.

FIG. 6 illustrates an alternate embodiment of the system MPDDS according to an embodiment of the present invention. Similar to the system 400 described in FIG. 4, the system 600 may include a pixel 610, column sample circuit 620, a comparator 606, and a column latch 630. Biasing transistor 605 may bias pixel 610 based on bias signal vb. The pixel 610 may be a two transistor design with a row select transistor 614 connected to the source of a chemically-sensitive sensor 612. The drain of the chemically-sensitive sensor 612 may be coupled to a supply voltage Vdda. The source of the row select transistor 614 may output from the pixel 610 and couple to column sample circuit 620 and the biasing transistor 605. The column sample 620 may provide a readout circuit for reading out pixels 610. The column sample 620 may include transistors 621, 623, 624 and 629 (which form a mirrored current source), a sampling capacitor C1, a reset transistor 622, and current steering transistor 624. The comparator 606 may provide a comparison function for an input received from the column sample circuit 620 and a reference voltage Vramp. The comparator 606 may be a high gain amplifier with a low input-referred noise level. The comparator 606 may be connected to the column latch 630. The column latch 630 may be an SR-latch. The latch 630 may be reset with 'Latch_reset' and set with either latch_set or the output of the comparator. The output of the latch circuit 630 may feedback to the column sample 620.

In operation, the system 600 operates substantially the same as the system 400 described above. The system 600 may also operate according to the timing diagram of FIG. 5. A primary difference is the configuration of the column sample circuit 620 is different from the column sample circuit 420 (formed from transistors 421, 423-425, 427 and 429). In particular, the mirrored current source formed from transistors 621, 623, 624 and 629 for charging the sampling capacitor C1 is different. In FIG. 4, the current is redirected when the latch trips whereas the current is simply turned off in FIG. 6. Although either configuration allows for proper operation of the MPDDS system 600 or 400, the column sample 420 configuration of FIG. 4 has an advantage in that the current supplied to the circuit 400 during the cancellation period is constant. Constant current operation can reduce disturbances on the power supplies (not shown) that might otherwise corrupt other circuits performing the same operation. Another difference of the column sample circuit 620 may be the configuration of inverters 631 as compared to the inverters in column sample circuit 420. The inverter 631 configuration may provide additional delay as compared to the inverters in column sample circuit 420.

Two different mismatches that can occur are current mismatching and threshold mismatching. Using the above described double sampling method in a single (1) transistor embodiment of the pixel, the double sampling may be performed against current matching. In the single chemically-sensitive transistor pixel, an additional transistor(s) outside the pixel (referred to as characterization transistor) may be used to address mismatch; to the extent a characterization transistor is otherwise designed to be smaller than a chemically-sensitive transistor, the characterization pixel may be made larger to the approximate size of the chemically-sensitive transistor (excluding floating gate structure) to reduce mismatch. Signal samples (current or voltage) taken of the additional characterization transistor(s) may be used to characterize offsets and mismatches of the single chemically-sensitive transistor pixel. In the single transistor pixel embodiment, the additional transistors may be sampled to provide a reference sample that characterizes the pixel, and the pixel may be sampled. Specifically, the pixel current may be sampled, and the current switched to pass through the larger transistors outside the pixel, and the current through the large transistors may be sampled. The delta double sample may be taken between the pixel current in one sample and the characterization transistor current in another sample. Note that the threshold mismatching may be minimal.

Mismatch and offsets are removed without the cost of increased temporal noise. It should be noted that while the pixel-to-pixel mismatch is reduced, all other offsets in the signal path are removed. Other benefits may be, for example, low frequency noise (flicker noise) may reduced due to rapid double sampling. In addition to being capable of removing the offset at the signal path level, the offset may also be removed at the pixel 310 level for each individual pixel. Specifically, the 1/f noise in the comparator is reduced using delta double sampling because the interval between samples of the comparator is reduced by several orders of magnitude.

Although the invention has been described above with reference to specific embodiments, the invention is not limited to the above embodiments and the specific configurations shown in the drawings. The operation processes are also not limited to those shown in the examples. Those skilled in the art will appreciate that the invention may be implemented in other ways without departing from the sprit and substantive features of the invention. The present embodiments are therefore to be considered in all respects as illustrative and not restrictive. The scope of the invention is indicated by the appended claims rather than by the foregoing description, and all changes that come within the meaning and range of equivalency of the claims are therefore intended to be embraced therein.

Several embodiments of the present invention are specifically illustrated and described herein. Those skilled in the art may appreciate from the foregoing description that the present invention may be implemented in a variety of forms, and that the various embodiments may be implemented alone or in combination. In other instances, well-known operations, components and circuits have not been described in detail so as not to obscure the embodiments. It can be appreciated that the specific structural and functional details disclosed herein may be representative and do not necessarily limit the scope of the embodiments. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

What is claimed is:

1. A method for detecting a chemical reaction, the method comprising:
    inducing a chemical reaction within a well coupled to a chemically-sensitive transistor, the chemically-sensitive transistor selectively coupled to a circuit node via a select transistor;
    operating the select transistor in a first mode during a first time interval of the chemical reaction, and sampling a reference signal at the circuit node;
    operating the select transistor in a second mode during a second time interval of the chemical reaction, and sampling a sensor signal at the circuit node; and
    normalizing the sampled sensor signal using the sampled reference signal to produce an output signal.

2. The method of claim 1, wherein the select transistor is operating in the saturation region during the first time interval.

3. The method of claim 1, wherein:
    sampling the reference signal comprises charging a first node of a sampling capacitor to a voltage of the reference signal, and charging a second node of the sampling capacitor to a first predetermined voltage; and
    sampling the sensor signal at the circuit node comprises charging the first node of the sampling capacitor to a voltage of the sensor signal, thereby inducing a voltage change at the second node of the sensor signal changes due to a difference between the voltage of the sensor signal and the voltage of the reference signal.

4. The method of claim 1, wherein the select transistor is operating in the linear region during the second time interval.

5. The method of claim 1, wherein the chemically-sensitive transistor is operating in the saturation region during the second time interval.

6. The method of claim 1, wherein the chemical reaction establishes a voltage at a terminal of the chemically-sensitive transistor, and the select transistor connects the terminal of the chemically-sensitive transistor to the circuit node during the second time interval.

7. The method of claim 1, wherein the chemical reaction is a sequencing reaction.

8. The method of claim 1, wherein the reference signal indicates a threshold voltage of the select transistor, and the sensor signal indicates a threshold voltage of the chemically-sensitive transistor.

9. The method of claim 1, wherein the select transistor blocks coupling of a terminal of the chemically-sensitive transistor to the circuit node during the first time interval, and connects the terminal of the chemically-sensitive transistor to the circuit node during the second time interval.

10. The method of claim 1, wherein the select transistor selectively couples a first terminal of the chemically-sensitive transistor to the circuit node, and further comprising:
    providing a bias current through the select transistor and the chemically-sensitive transistor during the first time interval and the second time interval; and
    providing a bias voltage to a second terminal of the chemically-sensitive transistor.

11. The method of claim 10, wherein the bias current and the bias voltage establish the reference signal at the circuit node during the first time interval, and establish the sensor signal at the circuit node during the second time interval.

\* \* \* \* \*